United States Patent [19]

Globe

[11] 3,999,297
[45] Dec. 28, 1976

[54] STRESS BREAKER APPLIANCE

[76] Inventor: Harold Globe, 200 S. Carson Road, Beverly Hills, Calif. 90211

[22] Filed: July 21, 1975

[21] Appl. No.: 597,946

[52] U.S. Cl. .................................................. 32/5
[51] Int. Cl.² ..................................... A61C 13/22
[58] Field of Search ....................................... 32/5, 6

[56] References Cited

UNITED STATES PATENTS

| 1,693,845 | 12/1928 | Kellner et al. | 32/5 |
| 2,611,957 | 9/1952 | Baca et al. | 32/5 |
| 2,797,456 | 7/1957 | Zahn | 32/5 |
| 3,019,528 | 2/1962 | DePietro | 32/5 |

Primary Examiner—Robert Peshock
Attorney, Agent, or Firm—Ralph B. Pastoriza

[57] ABSTRACT

The stress breaker appliance includes a main portion for engaging a patient's teeth and a supporting portion for false teeth coupled to the main portion. The coupling is such that the supporting portion can move up and down relative to the main portion so that stress on the patient's abutment teeth which would be exerted during chewing if the supporting portion were rigidly secured to the main portion is avoided.

4 Claims, 5 Drawing Figures

STRESS BREAKER APPLIANCE

This invention relates generally to stress breaker appliances as used in dental work and more particularly to a stress breaker appliance having improved interconnecting means for avoiding stress on abuttment teeth in the patient's mouth during mastication.

BACKGROUND OF THE INVENTION

Where a patient retains a certain number of teeth but has lost other teeth, it is common practice to provide a removable appliance which will support false teeth in a proper position for cooperation with the existing teeth so that the patient can carry on normal chewing or masticating functions. The supporting portion of the appliance for the false teeth if rigidly secured to the remaining portion of the appliance secured to the abuttment teeth can result in stress when the false teeth are engaged by the opposing teeth during mastication. In other words, torque and stress components are transmitted through the appliance to the abuttment teeth to which the appliance is secured.

In view of the foregoing problem, it is common practice to provide what is known in the art as a "stress breaker" type of appliance. In this type of appliance, the portion secured to the abuttment teeth is not rigidly coupled to the supporting portion for the false teeth but rather relative motion between these two portions is permitted. As a consequence, stress is not transmitted to the abuttment teeth when pressure is brought to bear on the false teeth.

While presently available stress breaker appliances do serve to "break" the stress, there are still problems encountered with the interconnecting or coupling of the portions relatively movable to each other on the appliance. It will be appreciated that the relative motion must be guided in order to avoid "canting" of the false teeth relative to the abuttment teeth. Further, there should be definite stops or limits of the relative motion so that the interconnecting means cannot inadvertently come uncoupled. The interconnecting arrangements presently available are not all satisfactory in these respects. Moreover, they are relatively expensive to manufacture.

BRIEF DESCRIPTION OF THE PRESENT INVENTION

With the foregoing in mind, the present invention contemplates a vastly improved stress breaker appliance incorporating a unique interconnecting means between the movable portions which assure accurate motion to effect a break in the stress and yet avoid any looseness or tendency for canting or wobbling of the false teeth relative to the abuttment teeth. Further, the particular interconnecting structure of the present invention is relatively inexpensive to manufacture.

In accord with the basic inventive concept, there is provided a stress breaker appliance comprising an arch-shaped main portion configured to engage and be secured to various existing teeth in a patient's mouth. A supporting portion adapted to mount and hold false teeth is also provided together with interconnecting means coupling the supporting portion to one end part of the main portion for guided movement with respect to the main portion. The intercoupling means is so designed that the level of the supporting portion relative to the main portion may vary. The movement itself is constrained to a given direction generally normal to the plane of the arch of the patient's teeth. This movement is also limited from extending beyond the level of the main portion in the direction in which the patient's teeth extend.

In the preferred embodiment, the interconnecting means takes the form of a wedge-shaped member secured to the main portion of the appliance and a wedge-shaped socket defined in the supporting portion for the false teeth, the wedge-shapes both being tapered so as to prevent movement of the wedge-shaped socket off the end of the wedge-shaped member. The geometry is such as to provide the desired constraining of the movement to the given direction so that canting or wobbling is minimized.

Further cooperating interconnecting means are provided in various modifications for special situations of the appliance.

BRIEF DESCRIPTION OF THE DRAWINGS

A better understanding of this invention will be had by now referring to the accompanying drawings in which.

DETAILED DESCRIPTION OF THE INVENTION

Figures 1, 2, 3, 4, 5:
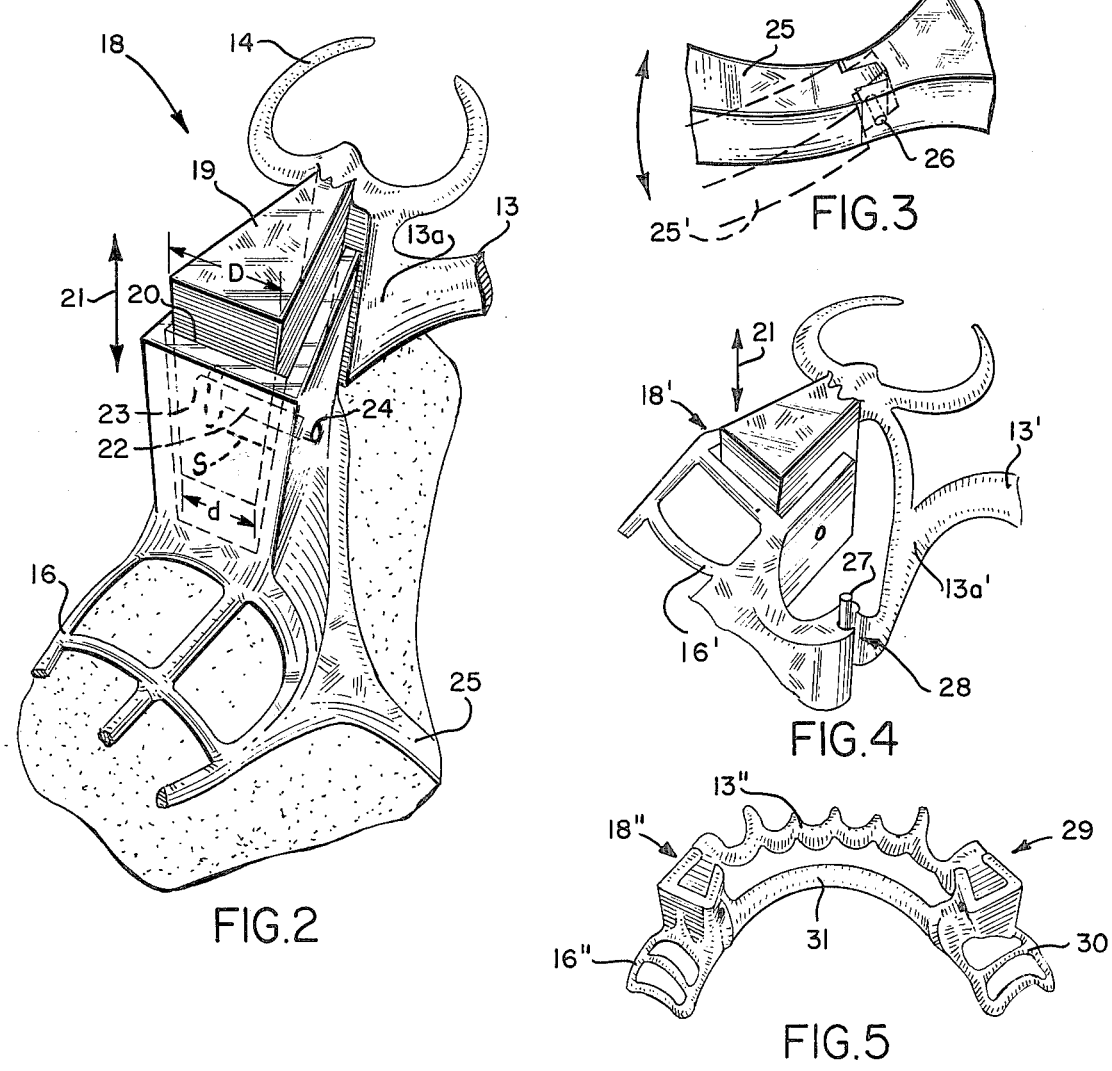
FIG. 1 is an exploded perspective view of a casting made from a patient's teeth and a stress breaker appliance shown above the cast preparatory to being positioned thereon incorporating features of the present invention.
FIG. 2 is a greatly enlarged fragmentary perspective view of that portion of the appliance enclosed within the circular arrow 2 of FIG. 1.
FIG. 3 is another fragmentary perspective view of a portion of the appliance enclosed within the circular arrow 3 of FIG. 1.
FIG. 4 is a fragmentary perspective view of a modified type of interconnecting means for the appliance; and, FIG. 5 is a fragmentary perspective view of a further modified appliance configuration in accord with the present invention.

Referring first to FIG. 1 there is shown a cast 10 representative of a patient's arch and teeth, there being indicated existing teeth at 11 and vacant gum areas where former teeth have been removed.

Shown exploded above the teeth is a stress breaker appliance designated generally by the numeral 12 comprising an arch-shaped main portion 13 configured to engage and be secured to various existing teeth in a patient's mouth. Towards this end there are provided encircling band portions such as indicated at 14 and 15.

A supporting portion 16 is provided and adapted to mount and hold false teeth, representative of such false teeth being indicated at 17 in exploded view above the supporting portion 16.

It will be appreciated that with the appliance secured to the patient's abuttment teeth, if the supporting portion 16 for the false teeth were rigidly secured to the main portion 13, when a patient chewed or exerted pressure on the false teeth, stresses would be transmitted to the abuttment teeth 11. On the other hand, such stresses can be "broken" by providing a suitable interconnecting means between the supporting portion 16 and main portion 13, permitting relative movement between these portions.

Such an interconnecting means is designated generally by the arrow 18 in FIG. 1 designed in accord with the present invention.

Referring now to FIG. 2, there is shown in enlarged perspective view the interconnecting means 18 of FIG. 1 wherein this means includes a wedge-shaped member 19 integrally formed on one end part 13a of the main portion 13. A cooperating wedge-shaped socket 20 in turn is defined on the supporting portion for receiving the wedge-shaped member 19. The arrangement is such that the wedge-shaped socket 20 can slide along the member 19 in a given direction indicated by the double-headed arrow 21.

In accord with the specific embodiment disclosed in FIG. 2, both the wedge-shaped member 19 and the wedge-shaped socket 20 taper in at least one dimension in a direction opposite to that in which the patient's teeth extend when the appliance is in place to thereby limit such sliding movement of the wedge-shaped socket from extending beyond the upper end of the wedge-shaped member as viewed in FIG. 2. As a specific example, this dimensioning might be the width of the wedge-shape indicated at D for the upper end of the member 19. The tapering in a downward direction as viewed in FIG. 2 results in a lesser dimension d at the lower end of the wedge-shaped member 19.

The socket 20 is similarly configured such that the socket cannot slide upwardly beyond a level coextensive with the top surface of the wedge shaped member 19.

Also provided in the preferred embodiment of this interconnecting means is a transverse pin 22 extending through a slot S in the wedge-shaped member 19. The wedge-shaped socket 20 in turn has opposite openings 23 and 24 within which the ends of the pin are secured. The slot S in the wedge is elongated to extend in the given direction of the double-headed arrow 21. This slot receives the pin 22 so that the main portion 13 is coupled to the supporting portion 16 and relative movement of the socket and wedge is limited to a distance defined by the length of the slot.

In the specific stress breaker appliance described in FIGS. 1 and 2, there is included a bridging arm 25 extending from the supporting portion 16 to the other end part of the arch-shaped main portion, this other end part being designated 13b in FIG. 1. In other words, this arm extends from the supporting portion to the end opposite the referred to one end 13a to which the supporting portion is coupled. The connection of the extending end of the arm 25 to the referred to other end portion 13b takes the form of a hinge means.

Referring specifically to the fragmentary view of FIG. 3, this hinge means is shown at 26 and permits hinging or swinging movement of the arm to accommodate movement of the supporting portion 16 in the given direction of the double-headed arrow 21 of FIG. 2. In FIG. 3, this motion is indicated in phantom lines at 25'.

Essentially, the provision of the extending arm 25 further stabilizes the constraining of the motion in the given direction of the arrow 21 to the desired direction generally normal to the plane of the arch of the patient's teeth. The motion is essentially vertical as viewed in FIGS. 1 and 2 but in actuality will be slightly arcuate as a consequence of the hinging of the arm 25. However, this arcuate motion is almost negligible over the small distance that the motion takes place.

Referring now to FIG. 4, there is shown a modified embodiment of the appliance wherein numerals are used to designate corresponding parts but are followed by a prime. In this modified form, rather than an extending arm such as 25 described with respect to the appliance of FIGS. 1, 2 and 3, there is provided a stabilizing guide in the form of a guide rail 27 secured to the main portion 13' adjacent to the one end 13a' of the modified appliance. The positioning is adjacent to the wedge-shaped member and the direction of the rail extends substantially parallel to the desired given direction of relative movement of the wedge and corresponding socket making up the interconnecting means 18' as again indicated by the double headed arrow 21.

Cooperating with the rail 27 is a guide channel 28 secured to the supporting portion 16', this guide channel receiving the guide rail to provide further constraining of the movement of the supporting portion to the desired given direction indicated by the double-headed arrow 21.

FIG. 5 shows a further modified stress breaker appliance wherein again corresponding portions are designated by the same numerals utilized in FIGS. 1 to 3 but followed by a double prime. This appliance is used where false teeth are required on both sides of the patient's jaw such that there is provided an additional interconnecting means 29 for an additional supporting portion 30. The supporting portion 30 is rigidly connected to the supporting portion 16'' by a cross structure 31. The interconnecting means 29 comprises a wedge-shaped member and wedge-shaped receiving socket similar to the interconnecting means 18 described in FIG. 2 and designated 18'' in FIG. 5.

With the foregoing arrangement, it will be appreciated that the supporting portions 16'' and 30 will move in the desired given direction; that is, in an up and down direction as viewed in FIG. 5 relative to the main portion 13'' of the appliance together as a unit. There is thus provided a cross stabilization for the desired motion.

The present invention thus provides three basic types of stress breaker appliances the selection of any one of the three types depending upon the requirements of the patient's mouth.

In all of the embodiments, the unique wedge-shaped member and cooperating wedge-shaped socket permit the desired relative movement of the supporting portion and main portion of the appliance to completely eliminate stress which would otherwise exist if these portions were rigidly secured.

The actual manufacture of the interconnecting means is greatly simplified by using simple lost wax casting techniques and a substantial savings in manufacturing cost is realized.

For example, a thin metal shim shaped to define the desired wedge through which the pin such as pin 22 in FIG. 2 is passed serves as a mold for both the wedge and socket which are cast about the shim and pin simultaneously. The shim is then removed by acid leaving the wedge and socket defining the interconnecting means.

From the foregoing description, it will accordingly be evident that the present invention has provided an important advance in the art of stress breakers used in dentistry.

What is claimed is:

1. A stress breaker appliance comprising:
   a. an arch-shaped main portion configured to engage and be secured to various abuttment teeth in a patient's mouth;
   b. a supporting portion adapted to mount and hold false teeth;

c. interconnecting means including a wedge shaped member on said main portion and a wedge shaped socket defined on said supporting portion receiving said wedge shaped member for sliding movement therealong, said wedge shaped member and wedge shaped socket tapering in at least one dimension in the direction opposite to that in which the patient's teeth extend to thereby limit said sliding movement of said wedge shaped socket from extending beyond one end of said wedge-shaped member such that the level of said supporting portion relative to said main portion may vary, said sliding movement being constrained to a given direction generally normal to the plane of the arch of said patient's teeth whereby stress on the patient's abuttment teeth which would be exerted during mastication if said supporting portion were rigidly secured to said main portion, is avoided; and d. a transverse pin extending through said wedge shaped member, with its ends secured to the socket, said wedge-shaped member having a slot extending generally in said given direction receiving the pin so that said main portion is coupled to said supporting portion and relative movement of the socket and wedge is limited to a distance defined by the length of the slot.

2. A stress breaker according to claim 1, including a bridge arm extending from said supporting portion to the other end part of said arch shaped main portion opposite the said one end part to which said supporting portion is coupled; and hinge means hinging said arm to said other end part for swinging movement to accommodate movement of said supporting portion in said given direction.

3. A stress breaker according to claim 1, including a guide rail secured to said one part on said main portion adjacent to said wedge shaped member extending in a direction parallel to said given direction; and a guide channel secured to said supporting portion receiving said guide rail to provide further constraining of the movement of said supporting portion in said given direction.

4. A stress breaker according to claim 1, including an additional supporting portion and an additional interconnecting means coupling said additional supporting portion to the other end part of said arch shaped main portion for guided movement with respect to said main portion, said additional interconnecting means being similarly constructed to said first mentioned interconnecting means whereby said additional supporting portion is guided for movement in a direction parallel to said given direction.

* * * * *